(12) United States Patent
McNair

(10) Patent No.: US 12,089,966 B1
(45) Date of Patent: Sep. 17, 2024

(54) ON-SCENE AND PRE-HOSPITAL RISK EVALUATION (OSPRE)

(71) Applicant: CERNER INNOVATION, INC., Kansas City, KS (US)

(72) Inventor: Douglas S. McNair, Seattle, WA (US)

(73) Assignee: Cerner Innovation, Inc., Kansas City, MO (US)

( * ) Notice: Subject to any disclaimer, the term of this patent is extended or adjusted under 35 U.S.C. 154(b) by 710 days.

(21) Appl. No.: 16/813,083

(22) Filed: Mar. 9, 2020

Related U.S. Application Data

(63) Continuation of application No. 13/569,808, filed on Aug. 8, 2012, now abandoned.

(60) Provisional application No. 61/521,223, filed on Aug. 8, 2011.

(51) Int. Cl.
*A61B 5/00* (2006.01)
*A61B 5/0205* (2006.01)

(52) U.S. Cl.
CPC .......... *A61B 5/7275* (2013.01); *A61B 5/0022* (2013.01); *A61B 5/0024* (2013.01); *A61B 5/0205* (2013.01); *A61B 5/6813* (2013.01); *A61B 5/7264* (2013.01); *A61B 2505/01* (2013.01)

(58) Field of Classification Search
CPC ... A61B 5/7275; A61B 5/0022; A61B 5/0024; A61B 5/0205; A61B 5/6813; A61B 5/7264; A61B 2505/01
USPC ......................................................... 705/2–3
See application file for complete search history.

(56) References Cited

U.S. PATENT DOCUMENTS

| | | | |
|---|---|---|---|
| 6,117,073 A | 9/2000 | Jones et al. | |
| 6,458,085 B1 | 10/2002 | Wu et al. | |
| 7,412,395 B2 | 8/2008 | Rowlandson | |
| 7,761,309 B2 * | 7/2010 | Sacco | G16H 50/50 |
| | | | 705/2 |
| 7,899,682 B2 | 3/2011 | Sacco et al. | |
| 8,484,048 B2 | 7/2013 | Halsted et al. | |
| 8,489,419 B2 * | 7/2013 | Sacco | G16H 10/60 |
| | | | 705/2 |
| 10,431,336 B1 | 10/2019 | Murrish et al. | |
| 2001/0044732 A1 | 11/2001 | Maus et al. | |
| 2004/0122296 A1 | 6/2004 | Hatlestad et al. | |

(Continued)

*Primary Examiner* — Michael Tomaszewski
(74) *Attorney, Agent, or Firm* — Kilpatrick Townsend & Stockton LLP

(57) ABSTRACT

System, methods and computer-readable media are provided for facilitating decision support by assessing the severity of injuries and the acute risk of physiologic deterioration and short-term mortality in trauma patients, both on the scene where emergency medical personnel initially evaluate and treat trauma victims and while in-transit to receive care at a health care facility. Embodiments of the invention provide a quantitative numerical score and calculated probabilities of deterioration and/or mortality, based on multi-variable statistical regressions. In some embodiments, fuzzy-set mathematics are employed in the regressions to account for physiologic and epistemologic uncertainty that are inherent in one or more emergency personnel members' observations and recordings of a plurality of measurements periodically during the time on-scene and during transit. Embodiments also enable the prediction of the other outcomes of trauma patients, such as the intensity of care that will likely be required prior to hospital arrival.

19 Claims, 9 Drawing Sheets

(56) References Cited

U.S. PATENT DOCUMENTS

| | | |
|---|---|---|
| 2005/0177393 A1 | 8/2005 | Sacco et al. |
| 2007/0112275 A1 | 5/2007 | Cooke et al. |
| 2008/0126124 A1 | 5/2008 | Schechter |
| 2009/0177495 A1 | 7/2009 | Abousy et al. |
| 2010/0030035 A1 | 2/2010 | Chan et al. |
| 2018/0113987 A1* | 4/2018 | Zhu .................. G16H 50/20 |
| 2018/0300540 A1* | 10/2018 | Swisher ............... G06N 3/08 |

* cited by examiner

| ON-SCENE & PRE-HOSPITAL RISK EVALUATION (OSPRE) SCORE | ENTER |
|---|---|
| EVALUATING A PRE-HOSPITAL EMERGENCY TRANSPORT PATIENT? (Y OR N) | Y |
| AGE PROBABLY BETWEEN 10 AND 70 YEARS? (Y OR N) | Y |
| EXPECTED SCENE-TO-HOSPITAL TRANSPORT TIME (MINUTES) | 26 |

300, 310

| ENTER AN "X" IN THE APPROPRIATE COLUMN FOR EACH QUESTION (GIVE ONLY 1 ANSWER PER ROW) | | | | | |
|---|---|---|---|---|---|
| PERFUSION & CARDIAC FUNCTION | | | | | |
| HEART RATE (BPM) | 50 - 140 | 141 - 180 X | 35 - 49 | > 180 | < 35 |
| 5-MIN HEART RATE VARIABILITY (1/SDNN, BPM) | > 1.0 | 0.8 - 1.0 | 0.5 - 0.7 X | 0.2 - 0.4 | < 0.2 |
| SYSTOLIC BLOOD PRESSURE (MMHG) | > 89 | 76 - 89 X | 50 - 75 | 30 - 49 | < 30 |
| 5-MIN SYSTOLIC BLOOD PRESSURE VARIABILITY (SDSBP, MMHG) | 50 - 140 | 141 - 180 X | 35 - 49 | > 180 | < 35 |
| OXYGENATION & RESPIRATORY FUNCTION | | | | | |
| SPO2 | < 95% | 89 - 95% X | 81 - 88% | 75 - 80% | < 75 |
| RESPIRATORY RATE (SPONTANEOUS BREATHING, BPM) | 11 - 30 | > 30 | 0.5 - 0.7 X | 1 - 5 | 0 |
| 5-MIN RESPIRATORY RATE VARIABILITY (1/SDIBI, BPM) | 0.8 - 1.3 | > 1.3 X | 0.6 - 0.8 | 0.4 - 0.6 | < 0.4 |
| TRAUMA & TISSUE INJURY | | | | | |
| BLUNT TRAMA | ABSENT | MILD | MODERATE X | SEVERE-FOCAL | SEVERE-EXTENSIVE |
| PENETRATING TRAUMA | ABSENT | MILD X | MODERATE | SEVERE-FOCAL | SEVERE-EXTENSIVE |
| THERMAL INJURY – BURNS | ABSENT X | MILD | MODERATE | SEVERE-FOCAL | SEVERE-EXTENSIVE |
| THERMAL STRESS – SYSTEMIC | 35°C < T < 38°C X | 32-35°C OR 38-39°C | 28-32°C OR 39-40°C | 20-28°C OR 40-41°C | T < 20°C OR > 41°C |
| INHALATION INJURY | ABSENT X | POSSIBLE | MILD | MODERATE | SEVERE |
| BRAIN INJURY | ABSENT X | MILD | MODERATE | SEVERE-FOCAL | SEVERE-EXTENSIVE |
| CEREBRAL FUNCTION | | | | | |
| REACTION LEVEL SCALE (RLS85) | 1 | 2 | 3 X | 4 | 5-8 |

320, 322, 324, 326, 328, 330

| CALCULATE | RESULTS |
|---|---|
| DATA COMPLETE? | Y |
| EVALUATION APPROPRIATE? | Y |
| OSPRE SCORE: 15 (OUT OF 56) OR 27% OF MAX | |

362, 364, 352, 354, 360

| PROB OF MORTALITY 24H POST-SCENE |
|---|
| 14% |

| TABLET DEVICE 📶 | MONDAY, AUGUST 8, 2011 | ✉ 100% 🔋 | | |
|---|---|---|---|---|
| ON-SCENE & PRE-HOSPITAL RISK EVALUATION (OSPRE) SCORE | | ENTER | | |
| EVALUATING A PRE-HOSPITAL EMERGENCY TRANSPORT PATIENT? (Y OR N) | | Y | | |
| AGE PROBABLY BETWEEN 10 AND 70 YEARS? (Y OR N) | | Y | | |
| EXPECTED SCENE-TO-HOSPITAL TRANSPORT TIME (MINUTES) | | 26 | | |
| ENTER AN "X" IN THE APPRPRIATE COLUMN FOR EACH QUESTION (GIVE ONLY 1 ANSWER PER ROW) | | | | |
| PERFUSION & CARDIAC FUNCTION | | | | |
| HEART RATE (BPM) | 50 - 140 | 141 - 180 | 35 - 49 | > 180 | < 35 |
| 5-MIN HEART RATE VARIABILITY (1/SDNN, BPM) | > 1.0 | 0.8 - 1.0 | 0.5 - 0.7 | 0.2 - 0.4 | < 0.2 |
| SYSTOLIC BLOOD PRESSURE (MMHG) | > 89 | 76 - 89 | 50 - 75 | 30 - 49 | < 30 |
| 5-MIN SYSTOLIC BLOOD PRESSURE VARIABILITY (SDSBP, MMHG) | 50 - 140 | 141 - 180 | 35 - 49 | > 180 | < 35 |
| OXYGENATION & RESPIRATORY FUNCTION | | | | |
| SPO2 | < 95% | 89-95% | 81 - 88% | 75 - 80% | < 75 |
| RESPIRATORY RATE (SPONTANEOUS BREATHING, BPM) | 11 - 30 | > 30 | 0.5 - 0.7 | 1 - 5 | 0 |
| 5-MIN RESPIRATORY RATE VARIABILITY (1/SDIBI, BPM) | 0.8 - 1.3 | > 1.3 | 0.6 - 0.8 | 0.4 - 0.6 | < 0.4 |
| TRAUMA & TISSUE INJURY | | | | |
| BLUNT TRAMA | ABSENT | MILD | MODERATE | SEVERE-FOCAL | SEVERE-EXTENSIVE |
| PENETRATING TRAUMA | ABSENT | MILD | MODERATE | SEVERE-FOCAL | SEVERE-EXTENSIVE |
| THERMAL INJURY - BURNS | ABSENT | MILD | MODERATE | SEVERE-FOCAL | SEVERE-EXTENSIVE |
| THERMAL STRESS - SYSTEMIC | 35°C < T < 38°C | 32-35°C OR 38-39°C | 28-32°C OR 39-40°C | 20-28°C OR 40-41°C | T < 20°C OR > 41°C |
| INHALATION INJURY | ABSENT | POSSIBLE | MILD | MODERATE | SEVERE |
| BRAIN INJURY | ABSENT | MILD | MODERATE | SEVERE-FOCAL | SEVERE-EXTENSIVE |
| CEREBRAL FUNCTION | | | | |
| REACTION LEVEL SCALE (RLS85) | 1 | 2 | 3 | 4 | 5-8 |

| CALCULATE | RESULTS | |
|---|---|---|
| DATA COMPLETE? | Y | PROB OF MORTALITY 24H POST-SCENE |
| EVALUATION APPROPRIATE? | Y | 14% |
| OSPRE SCORE: 15 (OUT OF 56) OR 27% OF MAX | | |

*FIG. 3B.*

| | A | B | C | D | E | F | G | H |
|---|---|---|---|---|---|---|---|---|
| 1 | ON-SCENE & PRE-HOSPITAL RISK EVALUATION (OSPRE) SCORE | ENTER | | | | | | |
| 2 | EVALUATING A PRE-HOSPITAL EMERGENCY TRANSPORT PATIENT? (Y OR N) | Y | | | | | | |
| 3 | AGE PROBABLY BETWEEN 10 AND 70 YEARS? (Y OR N) | Y | | | | | | |
| 4 | EXPECTED SCENE-TO-HOSPITAL TRANSPORT TIME (MINUTES) | 26 | | | | | | |
| 5 | | | | | | | | |
| 6 | ENTER AN "X" IN THE APPRIPRIATE COLUMN FOR EACH QUESTION (GIVE ONLY 1 ANSWER PER ROW) | | | | | | | |
| 7 | PERFUSION & CARDIAC FUNCTION | | | | | | | |
| 8 | HEART RATE (BPM) | 50 - 140 | 141 - 180 | 35 - 49 | > 180 | < 35 | | |
| 9 | | | X | | | | YES | 1 |
| 10 | 5-MIN HEART RATE VARIABILITY (1/SDNN, BPM) | > 1.0 | 0.8 - 1.0 | 0.5 - 0.7 | 0.2 - 0.4 | < 0.2 | | |
| 11 | | | | X | | | YES | 2 |
| 12 | SYSTOLIC BLOOD PRESSURE (MMHG) | > 89 | 76 - 89 | 50 - 75 | 30 - 49 | < 30 | | |
| 13 | | | X | | | | YES | 1 |
| 14 | 5-MIN SYSTOLIC BLOOD PRESSURE VARIABILITY (SDSBP, MMHG) | 50 - 140 | 141 - 180 | 35 - 49 | > 180 | < 35 | | |
| 15 | | | X | | | | YES | 1 |
| 16 | OXYGENATION & RESPIRATORY FUNCTION | | | | | | | |
| 17 | SPO2 | < 95% | 89-95% | 81 - 88% | 75 - 80% | < 75 | | |
| 18 | | | X | | | | YES | 2 |
| 19 | RESPIRATORY RATE (SPONTANEOUS BREATHING, BPM) | 11 - 30 | > 30 | 0.5 - 0.7 | 1 - 5 | 0 | | |
| 20 | | | X | | | | YES | 2 |
| 21 | 5-MIN RESPIRATORY RATE VARIABILITY (1/SDIBI, BPM) | 0.8 - 1.3 | > 1.3 | 0.6 - 0.8 | 0.4 - 0.6 | < 0.4 | | |
| 22 | | X | | | | | YES | 1 |
| 23 | TRAUMA & TISSUE INJURY | | | | | | | |
| 24 | BLUNT TRAMA | ABSENT | MILD | MODERATE | SEVERE-FOCAL | SEVERE-EXTENSIVE | | |
| 25 | | | | X | | | YES | 2 |
| 26 | PENETRATING TRAUMA | ABSENT | MILD | MODERATE | SEVERE-FOCAL | SEVERE-EXTENSIVE | | |
| 27 | | | X | | | | YES | 1 |
| 28 | THERMAL INJURY – BURNS | ABSENT | MILD | MODERATE | SEVERE-FOCAL | SEVERE-EXTENSIVE | | |
| 29 | | X | | | | | YES | 0 |
| 30 | THERMAL STRESS – SYSTEMIC | 35°C < T < 38°C | 32-35°C OR 38-39°C | 28-32°C OR 39-40°C | 20-28°C OR 40-41°C | T < 20°C OR > 41°C | | |
| 31 | | X | | | | | YES | 0 |
| 32 | INHALATION INJURY | ABSENT | POSSIBLE | MILD | MODERATE | SEVERE | | |
| 33 | | X | | | | | YES | 0 |
| 34 | BRAIN INJURY | ABSENT | MILD | MODERATE | SEVERE-FOCAL | SEVERE-EXTENSIVE | | |
| 35 | | X | | | | | YES | 0 |
| 36 | CEREBRAL FUNCTION | | | | | | | |
| 37 | REACTION LEVEL SCALE (RLS85) | 1 | 2 | 3 | 4 | 5-8 | | |
| 38 | | | | X | | | YES | 2 |
| 39 | | | | | | | | |
| 40 | CALCULATE | RESULTS | | | | | | |
| 41 | DATA COMPLETE? | Y | | | | PROB OF MORTALITY | | |
| 42 | EVALUATION APPROPRIATE? | Y | | | | 24H POST-SCENE | | |
| 43 | OSPRE SCORE | 15 | OUT OF 56, OR | 27% | OF MAX | 14% | | |

FIG. 4A.

| | A | B | C | D | E | F | G | H |
|---|---|---|---|---|---|---|---|---|
| 1 | ON-SCENE & PRE-HOSPITAL RISK EVALUATION (OSPRE) SCORE | ENTER | | | | | | |
| 2 | EVALUATING A PRE-HOSPITAL EMERGENCY TRANSPORT PATIENT? (Y OR N) | Y | | | | | | |
| 3 | AGE PROBABLY BETWEEN 10 AND 70 YEARS? (Y OR N) | Y | | | | | | |
| 4 | EXPECTED SCENE-TO-HOSPITAL TRANSPORT TIME (MINUTES) | 26 | | | | | | |
| 5 | | | | | | | | |
| 6 | ENTER AN "X" IN THE APPROPRIATE COLUMN FOR EACH QUESTION (GIVE ONLY 1 ANSWER PER ROW) | | | | | | | |
| 7 | PERFUSION & CARDIAC FUNCTION | | | | | | | |
| 8 | HEART RATE (BPM) | 50 – 140 | 141 – 180 | 35 – 49 | > 180 | < 35 | NO | CHECK DATA |
| 9 | | | X | | X | | | |
| 10 | 5-MIN HEART RATE VARIABILITY (1/SDNN, BPM) | > 1.0 | 0.8 – 1.0 | 0.5 – 0.7 | 0.2 – 0.4 | < 0.2 | YES | 2 |
| 11 | | | | X | | | | |
| 12 | SYSTOLIC BLOOD PRESSURE (MMHG) | > 89 | 76 – 89 | 50 – 75 | 30 – 49 | < 30 | YES | 1 |
| 13 | | | X | | | | | |
| 14 | 5-MIN SYSTOLIC BLOOD PRESSURE VARIABILITY (SDSBP, MMHG) | 50 – 140 | 141 – 180 | 35 – 49 | > 180 | < 35 | YES | 1 |
| 15 | | | X | | | | | |
| 16 | OXYGENATION & RESPIRATORY FUNCTION | | | | | | | |
| 17 | SPO2 | < 95% | 89-95% | 81 – 88% | 75 – 80% | < 75 | YES | 2 |
| 18 | | | | X | | | | |
| 19 | RESPIRATORY RATE (SPONTANEOUS BREATHING, BPM) | 11 – 30 | > 30 | 0.5 – 0.7 | 1 – 5 | 0 | NO | CHECK DATA |
| 20 | | | | | | | | |
| 21 | 5-MIN RESPIRATORY RATE VARIABILITY (1/SDIBI, BPM) | 0.8 – 1.3 | > 1.3 | 0.6 – 0.8 | 0.4 – 0.6 | < 0.4 | YES | |
| 22 | | | X | | | | | |
| 23 | TRAUMA & TISSUE INJURY | | | | | | | |
| 24 | BLUNT TRAUMA | ABSENT | MILD | MODERATE | SEVERE-FOCAL | SEVERE-EXTENSIVE | YES | 2 |
| 25 | | | | X | | | | |
| 26 | PENETRATING TRAUMA | ABSENT | MILD | MODERATE | SEVERE-FOCAL | SEVERE-EXTENSIVE | YES | 1 |
| 27 | | | X | | | | | |
| 28 | THERMAL INJURY – BURNS | ABSENT | MILD | MODERATE | SEVERE-FOCAL | SEVERE-EXTENSIVE | YES | 0 |
| 29 | | X | | | | | | |
| 30 | THERMAL STRESS – SYSTEMIC | 35°C < T < 38°C | 32-35°C OR 38-39°C | 28-32°C OR 39-40°C | 20-28°C OR 40-41°C | T < 20°C OR > 41°C | YES | 0 |
| 31 | | X | | | | | | |
| 32 | INHALATION INJURY | ABSENT | POSSIBLE | MILD | MODERATE | SEVERE | YES | 0 |
| 33 | | X | | | | | | |
| 34 | BRAIN INJURY | ABSENT | MILD | MODERATE | SEVERE-FOCAL | SEVERE-EXTENSIVE | YES | 0 |
| 35 | | X | | | | | | |
| 36 | CEREBRAL FUNCTION | | | | | | | |
| 37 | REACTION LEVEL SCALE (RLS85) | 1 | 2 | 3 | 4 | 5-8 | YES | 2 |
| 38 | | | | X | | | | |
| 39 | | | | | | | | |
| 40 | CALCULATE | RESULTS | | | | | | |
| 41 | DATA COMPLETE? | NO | | | | PROB OF MORTALITY | | |
| 42 | EVALUATION APPROPRIATE? | INCOMPLETE DATA | | | | 24H POST-SCENE | | |
| 43 | OSPRE SCORE | INCOMPLETE DATA | OUT OF 56, OR | | #VALUE! OF MAX | #VALUE! | | |

FIG. 4B.

ON-SCENE AND PRE-HOSPITAL RISK EVALUATION (OSPRE)

CROSS REFERENCE TO RELATED APPLICATIONS

This application is a continuation of U.S. patent application Ser. No. 13/569,808, titled "ON-SCENE AND PRE-HOSPITAL RISK EVALUATION (OSPRE)," filed Aug. 8, 2012, which claims the benefit of U.S. Provisional Application No. 61/521,223, titled "ON-SCENE AND PRE-HOSPITAL RISK EVALUATION (OSPRE)," filed Aug. 8, 2011, all of which is hereby expressly incorporated by reference in their entirety.

INTRODUCTION

Embodiments of the present invention are directed to the evaluation of illness and injury severity in patients who are being triaged by emergency medical personnel while on-scene and while in-transit to hospital. In particular, embodiments address the problem of trauma severity assessment. Prediction of the outcomes of trauma patients is presently compromised by only modest accuracy, and predictions for individual patients exhibit high rates of false-positive and false-negative predictions of mortality or other endpoints, such that the predictive models employed have limited usefulness for guiding specific interventions and care.

Accuracy and reliability of a monitoring system, among other things, depend on which parameters are being monitored, how many of the measurements can be made automatic without human intervention, and how representative the measurements are of the trends and fluctuations and evolution of the patient's parameters over time.

Several approaches to measurement of illness severity have been attempted with varying degrees of cost and reliability. Such approaches have been devised, however, without specific emphasis on the patient to be monitored being a trauma patient prior to and during transport to an acute-care hospital.

One category of illness-severity metrics is based on physiologic derangements. Nearly all of these scores have been directly or indirectly derived from the Acute Physiology and Chronic Health Evaluation (APACHE) score. The rationale is that derangements from physiologic norm are a measure of illness, and the more severe the derangements, the more severe the illness. In the APACHE model, 34 vital signs and laboratory results routinely available in the first 24 hours of admission are selected and weighted to form the APACHE. Higher scores were shown to correlate with death, morbidity, and resource use.

APACHE and other such scores have been revised and enhanced for application to trauma or surgical or other populations different from the in-hospital ICU populations for whom they were originally designed and calibrated. An apparent advantage of such physiology-based measures is that they are objective and seemingly reliable. However, a significant disadvantage is that their 95% prediction-intervals are so wide as to make them only reliable to apply to populations, and unreliable to apply to decisions about individual patients. Other such scores, including the TRISS, RTS, ASCOT, IATS, and others possess this same disadvantage, and while the use of the scores continues, explicit controlled studies increasingly reveal the unsafe or counter-productive hazards of their use.

Additionally, other predictive models were not designed to contemplate an environment with wearable sensors, personal area networks, and cheap continuous noninvasive digital monitoring technology. Thus, the parameters these models include in their predictions, and the frequency with which those parameters were measured and input, were constrained by practical limitations of manual human observation and data entry. However, there is increasing evidence that time-domain and/or frequency-domain measures of heart rate variability (HRV) and respiratory rate variability (RRV) are sensitive predictors of risk of physiologic deterioration.

Furthermore, other predictive models have been single-point-in-time point-estimates, generally produced from the observations and input of just one individual at one moment in time. However, it is common in trauma situations that multiple clinicians are involved in observing, assessing, and treating the patient over a period of some tens of minutes or more. Moreover, it is natural that the condition of the patient may evolve during this time; that the opportunities to make observations and measurements differ among these several clinicians, with the extent of the patient's injuries becoming progressively clearer as observation continues; and that the impressions and measurements and attributions of the several clinicians may also differ for valid reasons relating to their differing skills and experience.

Other approaches for addressing problems of trauma severity assessment have additional limitations including:

(1) Labor-intensiveness, giving rise to missed or hastily entered measurements that do not accurately represent the true condition of the patient, giving rise to either excessive false-positive Type I statistical error rates and over-prediction misclassification errors, or excessive false-negative Type II statistical error rates and under-prediction misclassification errors.

(2) Poor or absent accommodation of the measurements and assessments by multiple observers over a period of time.

(3) Failure to account for the partial, or intermittent, or uncertain observability of some of the parameters that are measured or assessed, at least at some points in time on-scene and in-transit, with the consequence that the models demand the user enter unrealistically precise values for parameters, where the underlying physiology has greater imprecision than what the models request.

(4) Lack of ability to adequately account for the observers' irreducible uncertainty and expressive doubt about the value of certain parameters' or variables' values at the times when measurements are being made, with the consequence that the models demand the user enter unrealistically precise values for parameters that cannot possibly be known with the precision specified.

(5) Lack of calibration for individual predictions (with, e.g., 95% prediction-interval limits) but only for population-level predictions (possibly with 95% confidence-interval limits).

(6) Calibration of mortality and other endpoints at 24 hour post-arrival, which confounds 'post-arrival' therapeutic/salvage maneuvers with 'on-scene' and 'in-transit' maneuvers.

(7) Lack of robustness against altitude and pitch-yaw-roll body-orientation attitude changes associated with flight.

With regard to the latter, it is cumbersome for a trauma predictive model to receive digital altitude or attitude information electronically. The applicant has found that detailed information of this type is in fact unnecessary, so long as relevant surrogate parameters denoting the magnitude and time-course of effects that changes in altitude and attitude have on the body (such as heart rate, heart rate variability, respiratory rate, respiratory rate variability, and reaction level) are measured and incorporated into the model.

(8) Dependence upon diastolic blood pressure (DBP), mean arterial pressure (MAP, depending on the combination of systolic blood pressure (SBP) and (DBP), or other parameters whose reliability and accuracy may be inferior to those of SBP owing to acoustical, mechanical vibration, or other environmental conditions on-scene or in-transit.

(9) Dependence on Fourier Transforms or Wavelet or other transforms to calculate spectral analytic parameters from timeseries or waveform signals, such that the size and cost of instruments capable of generating said transforms and analytics are in general scarcely compatible with the transport vehicle space and emergency medical service budget available.

(10) Dependence on Glasgow Coma Scale or other assessments of mental status and cognitive function that involve multi-step challenges from which the patient's response is excessively time-consuming to properly observe and record or that involve steps where the a patient's response is confounded or unobservable if the patient has been intubated or administered sedating, anxiolytic, or opioid analgesic agents, such that the score is either not possible to calculate or is inaccurate.

(11) Dependence on measuring urine output or other parameters that entail allowing many tens of minutes to elapse, during which no computation of the severity score is possible, until a measurable event (such as measurable micturition or Foley catheter output) occurs.

(12) Dependence on entering information about therapeutic interventions (such as crystalloid fluids, plasma expanders, or blood products administration) whose performance requires time to elapse, which thus either delays the computation of a score and prediction until the intervention has been completed or alternatively entails premature declaration by the user that the intervention has been accomplished when in fact it has not, with the result that the score may be inaccurate.

Accordingly, it is therefore valuable and highly desirable to provide systems and methods for providing decision support and evaluating illness and injury severity in patients who are being triaged while on scene and in transit to a health care facility which mitigates the aforementioned limitations.

SUMMARY

A system, methods and computer-readable media are provided for facilitating decision support by accurately and quickly determining the severity of injuries and the acute risk of physiologic deterioration and short-term mortality in trauma patients, both on the scene where emergency medical personnel initially evaluate and treat trauma victims and while in-transit to receive care at a health care facility. Embodiments of the invention determine severity of illness of a trauma patient, and in some embodiments further provide measurement of a mortality risk level of a transported trauma patient from the measure of illness severity.

In particular, embodiments of the invention provide a quantitative numerical score and calculated probabilities of deterioration and/or mortality, based on multi-variable statistical regressions. In some embodiments, fuzzy-set mathematics are employed in the regressions to account for physiologic and epistemologic uncertainty that are inherent in one or more emergency personnel members' observation and recordings of a plurality of measurements periodically during the time on-scene and during transit. Further, some embodiments have a design that directly incorporates the effects of duration of transport and young or advanced age, and indirectly incorporates into the model's predictions the effects of flight physiology affecting cardiovascular and pulmonary parameters. However, some embodiments are applicable to patients receiving ground transport as well as those receiving airborne transport. Embodiments also enable the prediction of the other outcomes of trauma patients, such as the intensity of care that will likely be required prior to hospital arrival.

Additional applications of embodiments of the invention provide a comparison of variations in outcomes and resources. And still other applications provide refinement and improvements. Further, in as much as embodiments provide the scoring system and method to classify illness severity in trauma patients prior to and during emergency transport to an acute-care hospital, embodiments also measure the degree of physiologic derangement across multiple organ systems, using vital signs and other information routinely recorded by emergency personnel.

In one example, aspect, system, method, and computer-readable media embodiments are provided for facilitating decision support by determining illness severity of a trauma patient who is a candidate for emergency transport to an acute-care facility, such as a hospital, in a time span. A time span for transport to the acute-care facility is determined. A plurality of measured values of a number N of various parameters are obtained from the patient during the time span and used to generate an optimal value for each N measured parameter. In some embodiments, the N parameters include one or more of mean approximate age, approximate anticipated transport time, heart rate, heart rate variability, systolic blood pressure, systolic blood pressure variability, respiratory rate, respiratory rate variability, peripheral blood oxygen saturation, blunt trauma, penetrating trauma, local thermal injury, systemic thermal stress, brain injury, inhalation injury, mental status, or similar available parameters. Fuzzy means are determined from one or more entries of the plurality of measured values for each of the N parameters from the patient being monitored. An indication of illness serenity of the patient is then determined by defuzzying and the fuzzy means for the N parameters and using the defuzzied means in a score calculation. In some embodiments, the severity indication is displayed and compared with other known values.

BRIEF DESCRIPTION OF THE DRAWINGS

Embodiments of the invention are described in detail below with reference to the attached drawing figures, wherein:

FIGS. 3A and 3B depicts illustrative examples of a graphical user interface (GUI) for receiving patient information and providing illness-severity analysis to a caregiver, in accordance with an embodiment of the invention; and FIGS. 4A and 4B depict screen shots of GUI from an embodiment of the invention reduced to practice with the GUI implemented in Microsoft Excel.

DETAILED DESCRIPTION

Figure 1A:
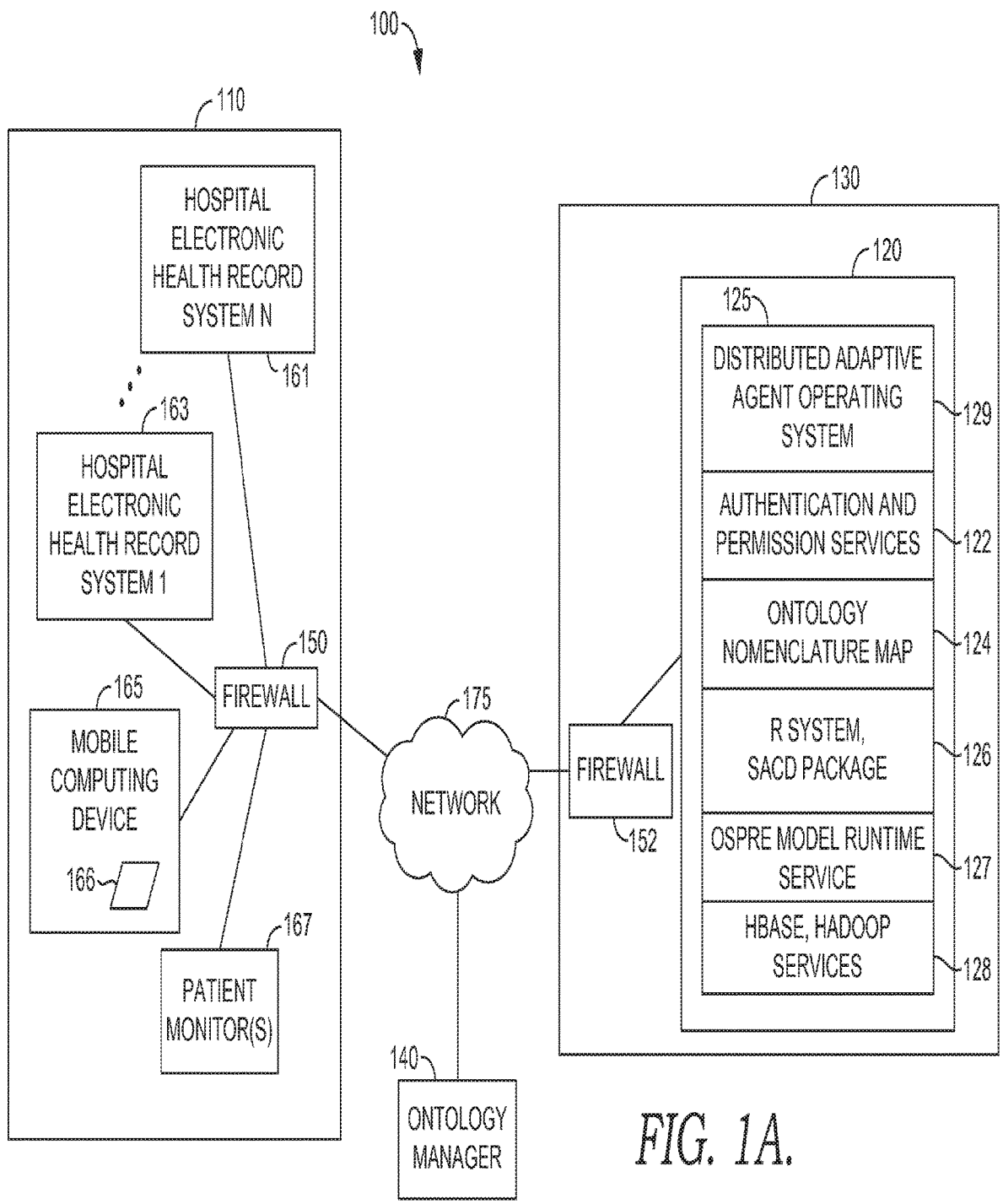
FIGS. 1A, 1B, and 1C depict aspects of an illustrative operating environment suitable for practicing embodiments of the invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplates media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

As discussed above, embodiments of the invention are provided for facilitating decision support by determining severity of illness and a measurement of a mortality risk level in trauma patients, both on the scene where emergency medical personnel initially evaluate and treat trauma victims and while in-transit to receive care at a health care facility. In particular, embodiments of the invention provide a quantitative numerical score and calculated probabilities of deterioration and/or mortality, based on multi-variable statistical regressions.

At a high level, the embodiments utilize a selection of parameters, which are related to information about a patient, that collectively comprise assessments of injuries and physiologic derangements. In some embodiments, a Reaction Level Score (RLS) is used for abstracting the level of consciousness and mental status. Alternatives (such as the Glasgow Coma Scale, for example) are far more difficult to assess, exhibit far lower statistical inter-observer agreement (especially in high-stress emergency situations), and are confounded by opioid analgesic administration and intubation.

Also used in embodiments is fuzzy arithmetic combining of a plurality of patient parameter measurements by the same observer or by multiple observers, over the course of on-scene and in-transit triage and evaluation of the patient. The fuzzy-set means of each of the parameters are defuzzified, and the crisp quantitative result for each is applied to a set of predictive equations to compute an On-Scene and Pre-hospital Risk Evaluation (OSPRE) score and to compute quantitative numeric values for each OSPRE outcome or endpoint.

Fuzzy set theory provides a suitable way to objectively and quantitatively account for epistemological and statistical uncertainties in the attributes and processes that are the subject of each of the multiple observations, and to account for uncertainties that arise from cognitive and behavioral phenomena in each observer. To date, the application of multi-observation empirical models in support of clinical assessment remains limited, in part due to information deficit and uncertainty regarding model parameters.

The defuzzification of convex polygonal fuzzy numbers is performed according to the following equation:

$$u^\circ = \frac{1}{(m+1)(m+1-i)^n} \sum_{i=0}^{m} \sum_{k=1}^{(m+1-i)^n} k_{\hat{u}}^{(i)}$$

where $k_{\hat{u}}^{(i)}$ denotes the kth element of the array $\hat{U}^{(i)}$ which is the array assigned to the ith membership level of the fuzzy number $$\hat{U} = \{\hat{U}^{(1)}, \ldots, \hat{U}^{(m)}\}$$

for uncertain fuzzy parameter U.

Turning now to FIG. 1A, there is presented in 100 an example operating environment suitable for practicing embodiments of the invention. Example operating environment 100 includes a computerized system for compiling and running an embodiment of a decision support recommendation service. With reference to FIG. 1A, a first premise location 110 includes a network behind firewall 150 communicatively coupled to network 175. In embodiments, network 175 includes the Internet, a public network, or a private network.

Premise location 110, which may comprise separate geographical locations, further includes one or more health record systems such, as for example, Hospital Electronic Health Record (EHR) System 1, shown as 163, through Hospital EHR System N 161, each communicatively coupled to network 175. In embodiments, Hospital EHR may also include other health records systems such as ambulatory Clinic Electronic Health Record System, Health Information Exchange Electronic Health Record System, or may be part of a larger EHR system. Embodiments of EHR systems 161 and 163 include one or more data stores of health records and may further include one or more computers or servers that facilitate the storing and retrieval of the health records. In some embodiments, EHRs 161 or 163 further support software information-management services, such as Cerner® Careware iBus, for receiving information from mobile device 165, patient monitor(s) 167 or other information sources. Additionally, embodiments of EHRs 161 and 163 may comprise a local or distributed network, which can include network 175, in some embodiments.

Firewall 150 might comprise a separate firewall associated with each health record system, in some embodiments, rather than a single firewall associated with premise 110, or may be absent in some embodiments. Furthermore, in some embodiments, one or more of the health record systems may be located in the cloud or may be stored in data stores that are distributed across multiple physical locations. In some embodiments, one or more health record systems are communicatively coupled to the cloud, which may include or be communicatively coupled to network 175. And in some embodiments, health record systems includes record systems which store real-time or near real-time patient information, such as wearable, bedside, or in-home patient monitors, for example.

Premise 110 further includes mobile computing device 165, communicatively coupled to network 175 and one or more of EHR systems 161 and 163. Mobile computing device 165 is usable by on-scene and in-transit emergency medical staff for receiving information about a trauma patient. In embodiments, mobile device 165 is communicatively coupled to network 175 and one or more HER systems 161 and 163 using a cellular, Wi-Fi, or similar wireless communication technologies. Furthermore, mobile device 165 may be embodied as a tablet computing device, smart phone, portable terminal, laptop computer, or other similar mobile device. In some embodiments, mobile device runs a software application 166 for receiving information about a patient, and in some embodiments, software application 166 is embodied as an app, applet, Web-based application, or local application running on mobile device 165. In some embodiments, application 166 includes a GUI for facilitating receiving patient information, such as the example user interfaces described in connection to FIGS. 3A and 3B. In particular, turning briefly to FIGS. 3A and 3B, example GUIs of software application 166 are illustratively provided. FIG. 3A shows example elements for one embodiment of a GUI for software application 166, generally referred to as 300. In embodiments, one or more on-scene or in-transit EMTs or caregivers assess and monitor the patient to obtain measurements of parameters such as, for example, blood pressure, temperature, urine output, bleeding, and evidence of other injuries. These parameter values are collected via monitor(s) 167 and/or software application 166 operating on mobile device 165 and, in some embodiments, registered on the computerized patient records. Accordingly, example GUI 300 includes elements 310, 320 and 350, which facilitate receiving and displaying patient-related information to a user/caregiver and inputting of patient-related information by a caregiver. For example, as discussed in connection to FIGS. 2A-2B, in some embodiments, a user or caregiver performs an assessment of the patient and enters information into elements of GUI 300. Further, in some embodiments, elements of GUI 300 prompt the user/caregiver for information to enter or enable the user to touch (via a touch-screen enabled mobile device 165) a location to enter information, as one might enter information into a touch-enabled tablet or smart phone. Some embodiments indicate onscreen where the user should enter the information, such as "ENTER," for example.

Example GUI 300 includes a first element 310, wherein the caregiver enters information about the patient including whether the evaluation is a pre-hospital emergency transport patient, whether the patient appears between 10 and 70 years old or the approximate age of the patient, and an expected scene-to-hospital time span or a time-to-arrival at a hospital or other acute care facility. In some embodiments age is an important variable, but precise age is often not available to the caregiver or other EMT personnel. Accordingly, in some embodiments, the OSPRE model uses a fuzzy ordinal variable for age, such as whether the age is probably between 10 and 70, as shown in the example of FIG. 3A.

As shown in element 310 of GUI 300, in some embodiments the user/caregiver provides information about the expected time of arrival, and in some embodiments, this value is determined by software application 166 using the location information of mobile device 165 and location information of the acute care facility. For example, application 166 can determine location of the mobile device 165 using location-identification functionality as described above in connection to FIG. 1A, and the velocity of the mobile device 165 using the same functionality, for example, by determining the change in device position over a period of time. Application 166 may receive information about the location of the acute care facility over network 175, from the vehicle, from a text message or other wireless communication, or it may be provided by the user/caregiver in some embodiments. In some embodiments, software application 166 updates estimated time of arrival throughout the transit.

GUI 300 further includes element 320, which also facilitates receiving or displaying information about a patient. Element 320 includes a triage assessment form to be performed by the user/caregiver on the patient. For example, as shown on the left-hand side of element 320 are various patient parameters such as heart rate (HR), respiratory rate (RR), systolic blood pressure (SBP), peripheral oxygen saturation (SpO2), blunt trauma, penetrating trauma, thermal injury, thermal stress, inhalation injury, brain injury, reaction level scale (RLS85), and variability of HR, RR, and SBP (in this example embodiment, a 5-minute time interval of HR, BB, and SBP variability is used, but other embodiments may use other times such as a 10-minute interval. Moreover, as described in connection to FIGS. 2A and 2B, this time may be determined based on the OSPRE entry time or the expected time-to-arrival at an acute care facility.) In particular, the example embodiment of FIG. 3A includes four areas of patient data for assessment: Perfusion and Cardiac Functions 322, Oxygenation and Respiratory Function 324, Trauma and Tissue Injury 326, and Cerebral Function 328. Embodiments using Cerebral Function 328 assessment, might utilize a simplified Reaction Level Scale (RLS85) or similar scale for assessing cerebral function.

Example element 320 includes five columns or contiguous zones 330 of assessment for each of the patient parameters. For example, heart rate includes five zones: 50-140, 141-180, 35-49, >180, and <35. In embodiments, zones 330 are ordinal ranges of the parameters and are used for fuzzy arithmetic. In particular, in some embodiments a reference database table (which may be embodied as a content-table parameter in a multi-agent operating system) stores an array of fuzzy weighting factors for each zone of the patient parameters. As described in connection to FIGS. 2A and 2B, the weighting factors are applied as multipliers for one or more predictive statistical equations of the endpoints or outcomes, such as a logistical regression equation for the probability of mortality within 24 hours after departing the trauma scene en route to an acute-care facility. Although five zones are shown in the example embodiment of GUI 300 for practicality and simplicity, other embodiments could have four or fewer zones or six or more zones.

In some embodiments a user/caregiver enters parameter values into the zones based on assessment, which can include observational and physiological assessments performed on the patient. In some embodiments, the user/caregiver reads patient data from one or more monitors 167 and enters it into the appropriate zone 330, and in some embodiments mobile device 165 receives patient data from monitor(s) 167 and automatically populates the appropriate zone. In some embodiments, the user/caregiver verifies the automatically populated patient data.

Example GUI 300 also includes element 350, which provides an OSPRE score 360 for the patient, a probability or mortality within 24-hours after arrival 370, or other output determinations. In some embodiments, element 350 also provides feedback to the user/caregiver in fields 352 and 354 regarding whether the data is complete and whether the evaluation is appropriate for the patient. For example, if a caregiver accidentally omitted assessing a parameter in element 320, then data complete field 352 would indicate that data was incomplete. An example of this error and feedback is provided and discussed in connection to FIG. 4B. Evaluation appropriate field 354 may also provide feedback about whether score 360 and 24-hour mortality probability 370 are any good, based on the information collected during the OSPRE entry.

In the example element 350, the OSPRE score 360 comprises a score (here "15" or "15 out of a maximum of 56"), which may also be provided as a percentage (here, "27% of max," which corresponds to 15/56). Generally the worse the patient's condition, the higher the OSPRE score. Example element 350 also includes a determination of 24-hour mortality probability 370. In some embodiments, score 360 and mortality probability 370 are each partial scores, updated with each successive OSPRE entry taken, as described in connection to FIGS. 2A and 2B. Thus in some embodiments, with each additional OSPRE entry, the score and probability are recomputed until the patient arrives at the acute care facility in which a final score and probability may be determined.

In embodiments, probability 370, which is expressed as a percentage in this example, and OSPRE score 360 can be used for preparing or scheduling resources at the acute care facility, or for ranking patients or otherwise determining priority of treatments for patients, as may be necessary in a mass casualty scenario where hospital resources and staff are limited.

FIG. 3B shows another example GUI, which is embodied as operating on an Apple® iPad® tablet computer.

Returning to FIG. 1A, in some embodiments, mobile device 165 further includes location-identifying functionality, such as global-positioning system (GPS) service, other software-based location services, or functionality for receiving location information from a user. In such embodiments, software application 166 operating on mobile device 165 can further include functionality for determining an estimated time-until-arrival at an acute health care facility, based on GPS or location services and/or information received over network 175, or from a user.

Premise 110 includes one or more patient monitors 167, communicatively coupled to network 175, mobile device 165, and/or one or more of EHR systems 161 and 163. Monitor 167 may comprise a plurality of patient monitors or sensors capable of monitoring, measuring, or receiving information about a patient. In some embodiments, monitor 167 receives patient information and communicates it to mobile device 165 and/or one or more EHR systems 161 and 163, in near-real time as the patient information is acquired, in bursts, or periodically. Examples of monitors 167 include ECG trachometry and non-invasive blood pressure telemetry and respiratory rate equipment such as a continuous digital ECG or plethysmographic sensor, vital signs and ECG patient-wearable monitors, such as the Visi® line of devices distributed by Sotera Wireless of San Diego, California, or monitor devices capable of measuring patent conditions such as continuous heart rate, heart-rate variability, continuous respiratory rate, respiratory-rate variability, or systolic blood pressure, for example. In some embodiments, the measurement output of monitor(s) 167 is accessible by mobile device 165, which displays for a user the patient information acquired by monitor(s) 167.

Continuing with FIG. 1A, example operating environment 100 further includes computer system 120 within premise 130, which may take the form of a server, and which is communicatively coupled through firewall 152 and network 175 to EHRs 161 and 163, mobile device 165, and monitor(s) 167, in premise location 110, and also to ontology manager 140. In embodiments, ontology manager 140 may take the form of a software application operating on one or more mobile computing devices, tablets, smart phones, front-end terminals in communication with a back-end computing system, laptops or other computing devices. In some embodiments ontology manager 140 includes a Web-based or cloud-based application or collection of applications that is usable to manage services provided by embodiments of the invention, and in some embodiments includes one or more software agents operating on a multi-agent computing system, as described below. Ontology manager 140 provides services for facilitating matching patient information, which may be received from different on-scene and in-transit caregivers such as EMTs or health care providers, using different record systems with differing ontologies, in some cases, or also received from EHRs 161 and 163. Ontology manager 140 facilitates matching ontologies including patient-identity matching, patient records, and synonymic matching. Further examples of such ontology managing services as contemplated in embodiments of the invention are provided in U.S. Provisional Application No. 61/544,919, filed on Oct. 7, 2011, which is herein incorporated by reference in its entirety. Moreover, some embodiments of ontology managing services disclosed in Provisional Application No. 61/544,919 are supported by U.S. patent application Ser. No. 13/250,072, filed on Sep. 30, 2011, which is incorporated by reference into Provisional Application No. 61/544,919. Accordingly, U.S. patent application Ser. No. 13/250,072, filed on Sep. 30, 2011, is herein incorporated by reference in its entirety. This same U.S. patent application Ser. No. 13/250,072 is also expressly incorporated into the present application below in connection with FIGS. 1A-1C.

Embodiments of computer system 120 include software stack 125, which runs on computer system 120 shown in FIGS. 1A and also 1B. Embodiments of software stack 125 may run as a distributed operating system on a virtualization layer within computer system 120. Some embodiments of software stack 125 include a distributed adaptive agent operating system 129, as described below, which can support a number of services such as services 122, 124, 126, 127, and 128. In some embodiments, one or more dedicated software agents handles these software services. Some embodiments of services 122, 124, 126, 127, and 128 run as a local or distributed stack on a collection of personal computers and servers such as 120 and/or a computing device running ontology manager 140 or mobile device 165. In one embodiment, ontology manager 140 and mobile device 165 operate in conjunction with software stack 125.

In embodiments, authentication and permission services 122 provide services that facilitate accessing and authenticating users of mobile device 165, such as an on-scene or in-transit caregiver, EMT, or other health care provider or OSPRE users. In some embodiments, services 122 perform patient-account services, including managing accessing permissions, verification, and authorization services associated with a patient's health record or patient information received from monitor(s) 167 and mobile device 165.

Ontology nomenclature map 124 provides ontology mapping services for supporting ontology manager 140 by facilitating matching patient information, which may be received from different on-scene and in-transit caregivers, using different record systems with differing ontologies, in some cases, or also received from HER systems 161 and 163.

Software packages 126 perform statistical software operations, and include statistical calculation packages such as, in one embodiment, the R system and R-system modules, and packages such as SACD for facilitating fuzzy arithmetic calculations and performing fuzzy-set evidence combining and statistical regressions. An example embodiment employing software packages 126 is described in connection to FIGS. 2A and 2B at steps 260 and 265. Software packages 126 are associated with embodiments of services 127, which carry out the OSPRE model runtime, and services 128 that include Apache Hadoop and Hbase framework for providing a distributed file system. Embodiments of OSPRE runtime service 127 may run on computer system 120 or mobile device 165, or run in the cloud and be distributed across system 120 and mobile device 165. OSPRE runtime service facilitates receiving patient information from one or more mobile devices 165 and monitor(s) 167 and determining a quantitative numerical score of illness severity and calculated probabilities of deterioration and/or mortality, based on multi-variable statistical regressions.

Figure 1B:
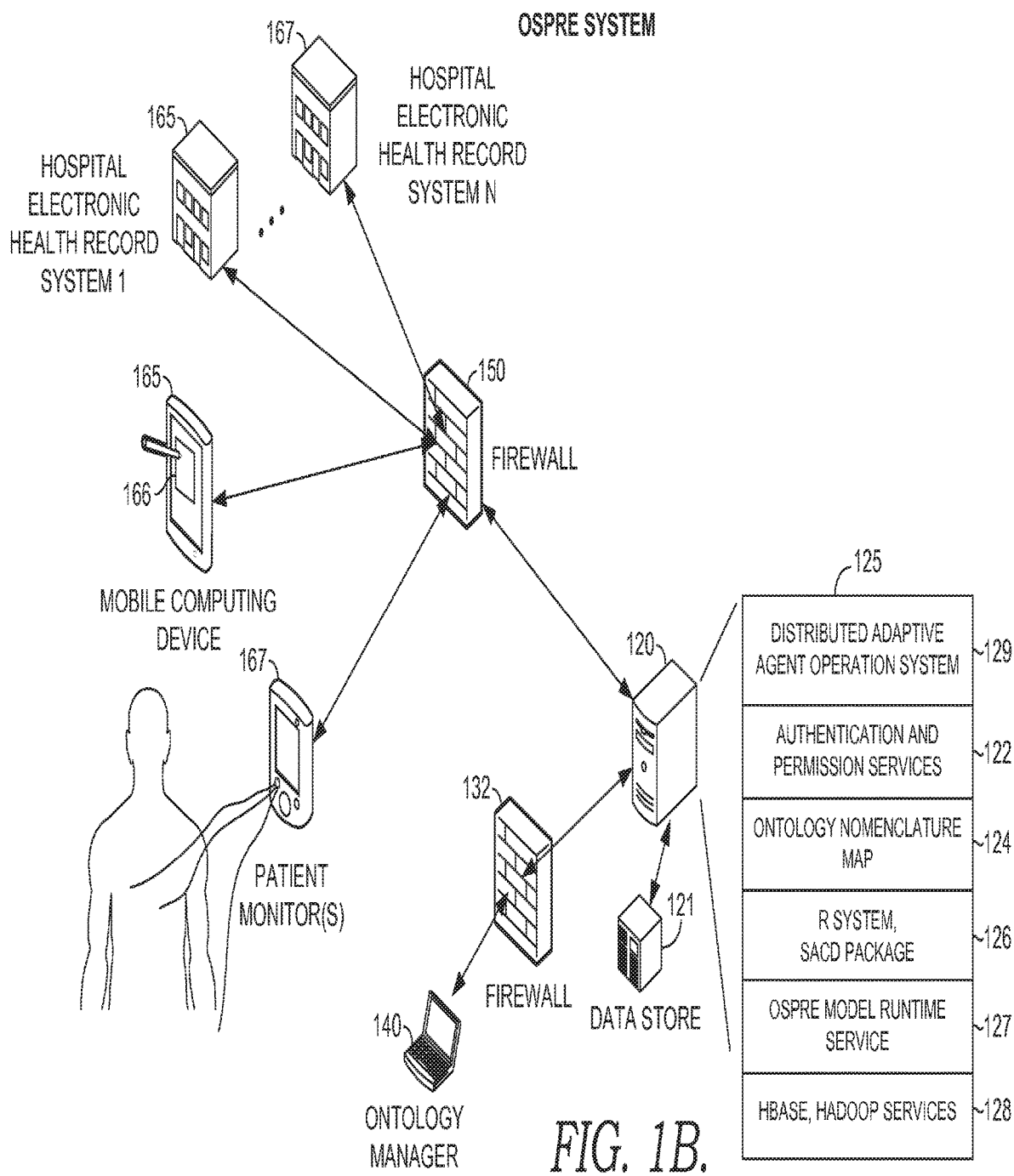

FIG. 1B illustratively depicts another aspect of an example operating environment. Some of the components of FIG. 1B are described above with respect to FIG. 1A. Also shown in FIG. 1B is data store 121, which in some embodiments includes patient data and patient information for one or more patients including information obtained from mobile device 165 and monitor(s) 167; parameters associated with operating system 129 and services 122, 124, 126, 127 and 128 including variables associated with recommendations; recommendation knowledge base; recommendation rules; recommendations; recommendation update statistics; operational data store, which stores events; frequent itemsets (such as "X often happens with Y", for example) and itemsets index information; association rulebases, agent libraries, and other information, patient-derived data, healthcare provider information, for example. Although depicted as a single data store, may comprise more than one data store one or multiple locations, or in the cloud. The example operating environment of FIG. 1B also includes a firewall 132 between ontology manager 140 and computer system 120.

Figure 1C:
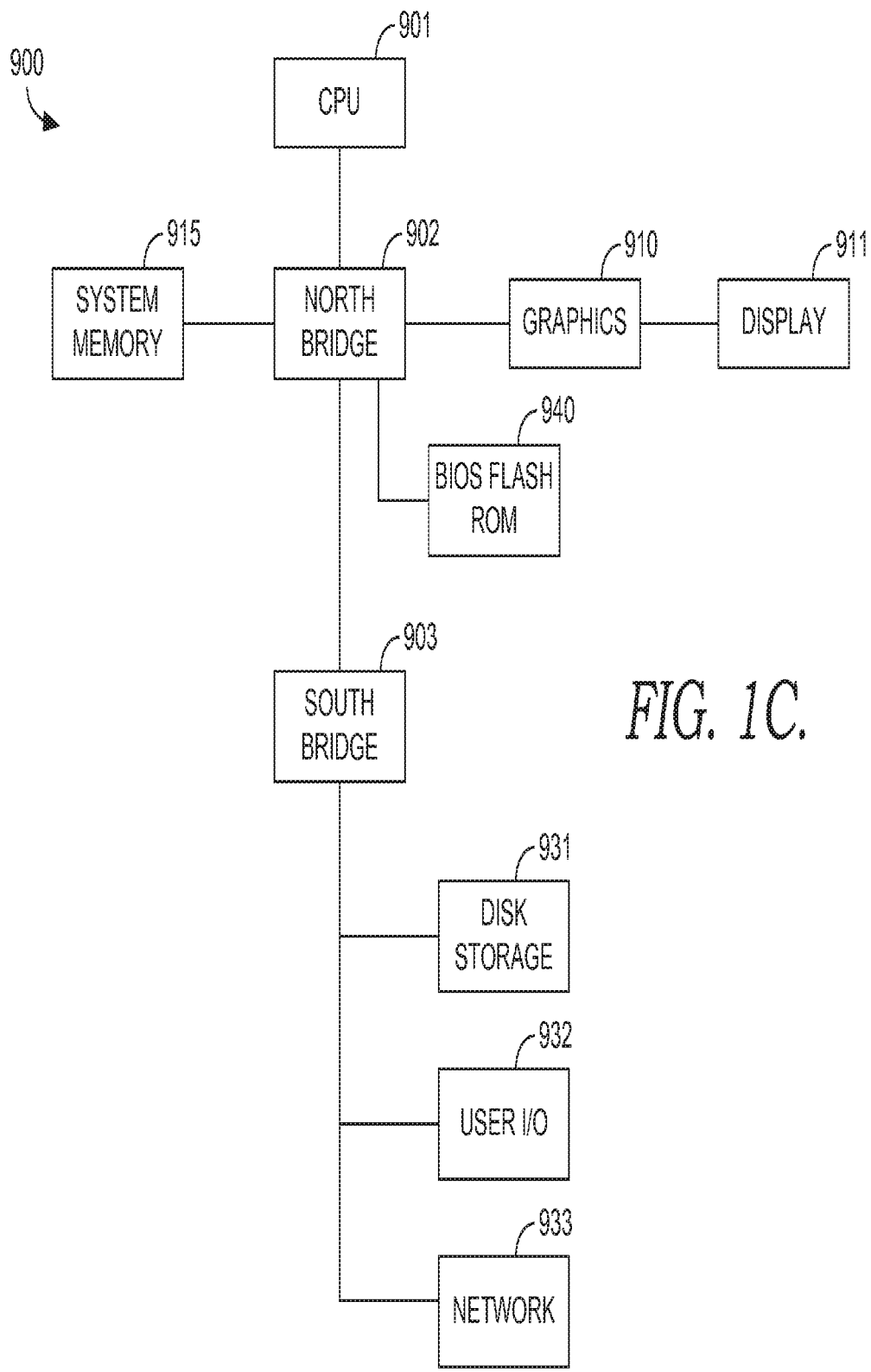

Turning now to FIG. 1C, there is shown one example of an embodiment of computer system 900 that has software instructions for storage of data and programs in computer-readable media. Computer system 900 is representative of a system architecture that is suitable for computer systems such as 120 and the computer device(s) operating ontology manager 140 and mobile device 165, in some embodiments. One or more CPUs such as 901, have internal memory for storage and couple to the north bridge device 902, allowing CPU 901 to store instructions and data elements in system memory 915, or memory associated with graphics card 910 which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU through south bridge 903 as well. The system architecture depicted in FIG. 1C is merely one example of any number of computer architectures suitable for supporting computer system 120 of FIGS. 1A and 1B.

In some embodiments, computing system 900 is a computing system made up of one or more computing devices. In an embodiment, computing system 900 includes an adaptive multi-agent operating system, but it will be appreciated that computing system 900 may also take the form of an adaptive single agent system or a non-agent system. Computing system 900 may be a distributed computing system, a data processing system, a centralized computing system, a single computer such as a desktop or laptop computer or a networked computing system.

In some embodiments, computing system 900 is a multi-agent computer system with software agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 2A:
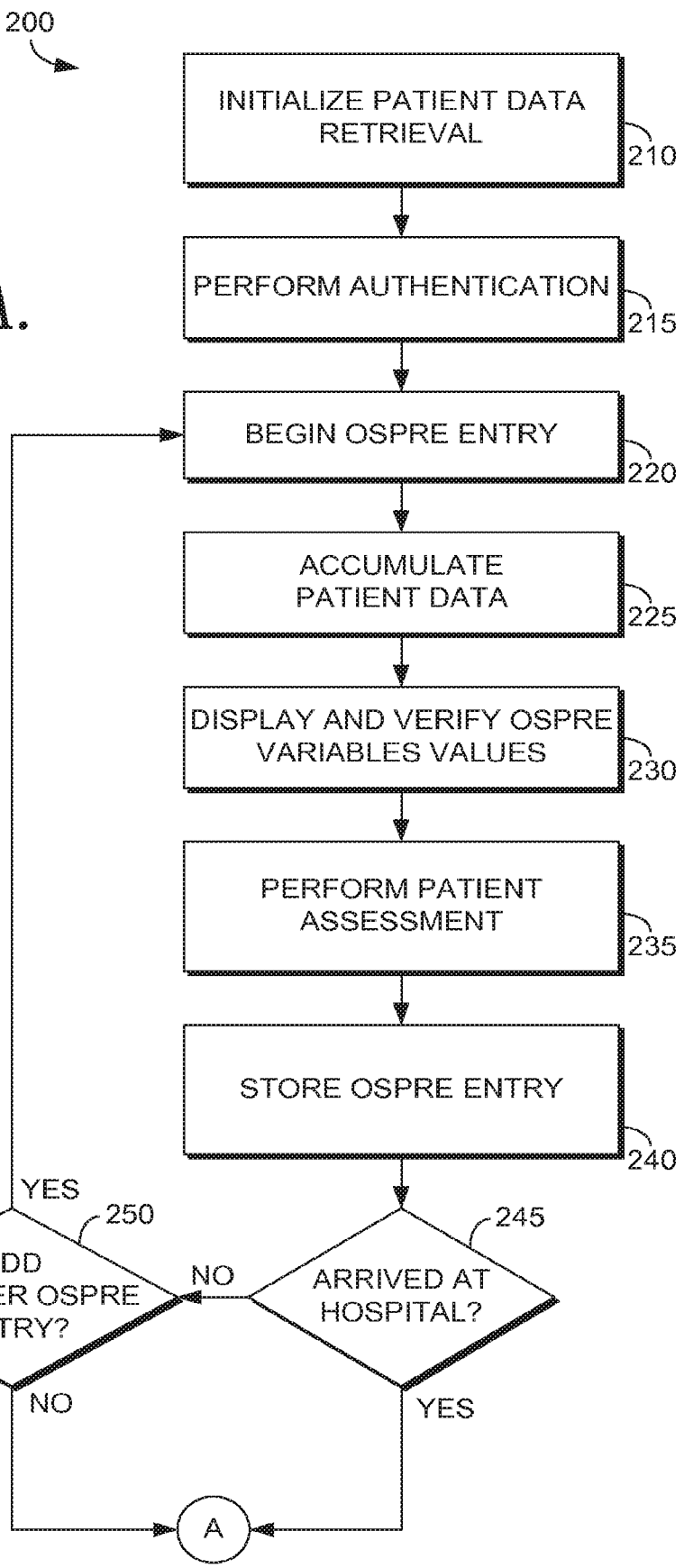
FIGS. 2A and 2B depict a flow diagram of a method for determining illness severity of a trauma patient, in accordance with embodiments of the invention.
Figure 2B:
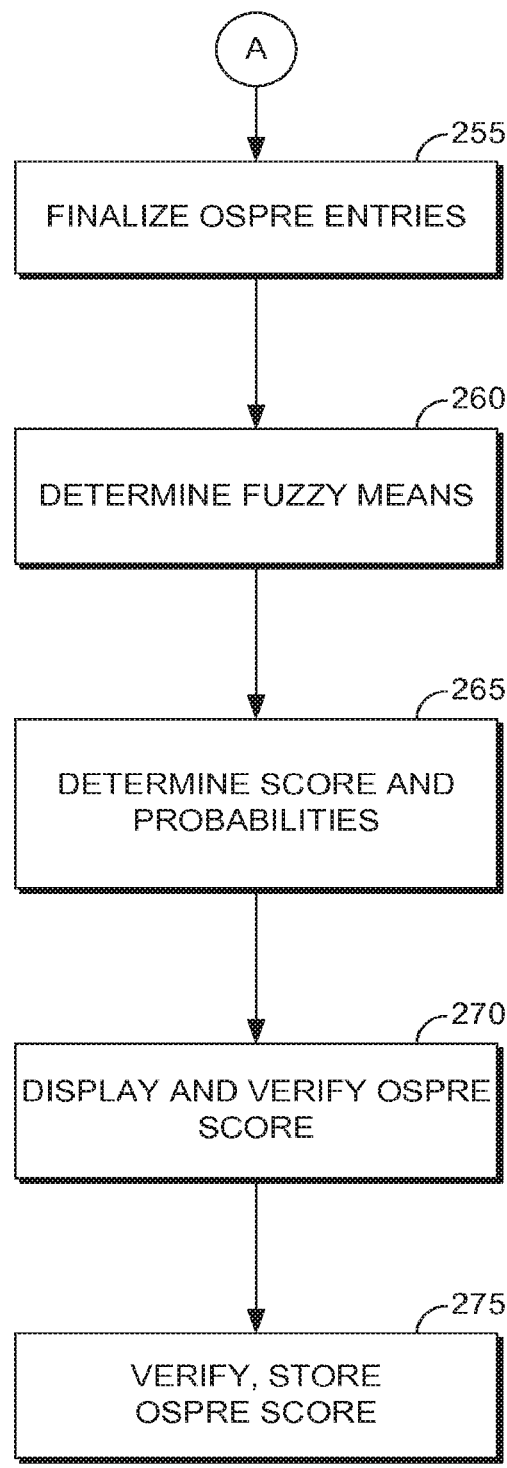

Referring now to FIGS. 2A and 2B, a flow diagram is provided of a method for determining severity of illness and a measurement of mortality risk level in trauma patients, in accordance with an embodiment of the invention, and which is generally referred to herein as 200. Embodiments of method 200 can be started when caregivers (such as emergency medical technicians (EMTs), medical staff, or other health care providers) arrive on-scene of a trauma patient and begin triage, and continue as the patient is transported to an acute care facility. At a step 210, patient-data retrieval is initialized. In some embodiments this step includes initializing one or more patient monitor(s) 167 and mobile device 165. In some embodiments, the patient is connected to monitor(s) 167, which might include fastening wearable sensors to the patient or placing sensors in proximity to the patient. Patient data retrieved by one or more monitor(s) 167 include, for example, continuous heart rate, heart-rate variability, continuous respiratory rate, respiratory-rate variability, peripheral oxygen saturation, systolic blood pressure, other vital signs or data associated with the patient's condition. In some embodiments, patient data is received by monitor(s) 167 continuously, periodically, or when new data is available, and in some embodiments it is communicated to mobile device 165 as it is received.

At a step 215, user authentication is performed. User authentication ensures that only permitted caregivers are accessing the OSPRE system or providing and viewing information about a patient, or in some embodiments the authentication associates a user/caregiver with an account for facilitating receiving information about the patient and monitoring and caring for the patient on-scene and in-transit. User authentication is facilitated by mobile device 165, in some embodiments. For example, a user such as an on-scene or in-transit caregivers, accesses a software application, running on mobile device 165, for entering patient information and monitoring the patient's condition. In some embodiments, the user is authenticated by providing identity-credentials. In some embodiments, the user/caregiver logs in to or accesses an account associated with the caregiver or associated with the patient. The account facilitates receiving patient-information, which may be received from a plurality of medical staff, and associating the received information with the patient. In one embodiment, the user/caregiver logs in to an account and provides patient information, which may include identifying information if the user/caregiver knows the identity of the patient, or may include a patient number or code created for his incident, and used for initializing an OSPRE session for that particular patient. In some embodiments, account information is used for identifying the health care provider, which information may be useful for follow-up with that on-scene or in-transit caregiver, or for facilitating ontology mapping, where it is known that the caregiver is associated with a particular health care institution, which uses a certain ontology.

Continuing with the method of FIGS. 2A and 2B, at a step 220, the method begins an OSPRE entry. In some embodiments an OSPRE entry comprises receiving a certain amount of patient information to be used for computing a partial OSPRE score over a time period of T minutes, where T may be 5 minutes or 10 minutes, for example. As described in connection to steps 245 and 250 below, the anticipated time for transporting the patient to the acute care facility can be discretized into T-minute time in some embodiments, such that an OSPRE entry may be performed over the T-minute interval. It is further contemplated in some embodiments that multiple OSPRE entries may be taken and used for determining a final OSPRE score. Accordingly, if at step 220, this is the first OSPRE entry for a particular patient, then a caregiver accesses a software application on mobile device 165 and begins receiving data from patient monitor(s) 167 or prepares mobile device 165 for receiving information from patient monitors 167, for example, by selecting which monitor(s) 167 are initialized from step 210, or by identifying the specific patient parameters (such as continuous and variable heart rate and respiratory rate, etc.) to be measured, in some embodiments. Moreover, in some embodiments, the software application operating on mobile device 165 interrogates the user for information regarding the types of monitor(s) 167 being used or which patient parameters are being measured. In some embodiments, the software application operating on mobile device 165 determines, without interrogating the user, which patient parameters are being measured based on information received from monitor(s) 167 or information received from computer system 120 over network 175.

If at step 220, this is not the first OSPRE entry for a particular patient, then at step 220 another OSPRE entry is started. In some embodiments, software application 166 operating on mobile device 165 displays an indication, such as a running count of OSPRE entries, for the current OSPRE session with the patient, which might benefit the caregiver, for example, by indicating that another OSPRE entry is underway. For example, the third OSPRE entry might display "OSPRE Entry=3 (of 6 estimated)", where the estimated total (here, six) is determined based on the T-minute interval of taking an OSPRE entry and an estimated time of arrival to the acute care facility, as described below in connection to steps 245 and 250.

Each OSPRE entry comprises receiving patient information, as described in connection to steps 220 through 240, for possible use in computing the OSPRE score. Accordingly, it is within the scope of embodiments of the invention to use any physical measurements and assessments, some of which can be made automatically and continuously, without human intervention, such as some of the data accumulated in step 225, as described below. Other assessments depend on human intervention and observation and values are entered by the human observer, such as the user/caregiver, by for example pointing gestures on a software graphical user interface on mobile device 165, in an embodiment or by other means. A total number "N" of different patient parameters to be monitored, measured, or assessed is identified. In some embodiments, software application 166 is initialized or configured to receive information on the N different patient parameters. In some embodiments this identification occurs in step 215, as described above.

At a step 225, patient information is accumulated from one or more patient monitors 167. In some embodiments, measurements of values for each of the N patient parameters are retrieved by one or more monitors 167 and fed into a buffer. Further, in embodiments, data is accumulated for a time interval T, such as 5 minutes or 10 minutes, corresponding to the duration of an OSPRE entry. In some embodiments, monitors(s) 167 communicate data to mobile device 165, which in some embodiments displays information derived from the data (such as heart rate, blood oxygen level or other patient parameters being measured or monitored by monitor(s) 167, for example) via a graphical user interface of software application 166. In one embodiment, patient data is accumulated from patient parameters including: heart rate (HR), heart rate variability (HRV), respirator rate (RR), respiratory-rate variability (RRV), and systolic blood pressure (SBP). In embodiments that perform measuring variability of heart rate and/or respiratory rate, time interval T is used for determining the measure of variability. Alternatively, in some embodiments, a different time interval that is a fraction of time interval T, may be used. For example, if T is 10 minutes, a T/2 or 5-minute interval may be used to determine RRV and HRV.

Additionally, in some embodiments, data accumulated in step 225 also includes environmental information such as, room or cabin temperature, altitude (which may also be associated with the type of vehicle transporting the patient, such as fixed-wing or helicopter), cabin pressure, number of patients in vehicle, number of caregivers attending to patients, caregiver(s) location and proximity with respect to patient, and time spent for each caregiver observing patient, for example. In some embodiments, this environmental information is received from sensors, such as a thermometer, altimeter, and barometer, which are in the vehicle used for transporting the patient, provided by the caregiver using mobile device 165, or obtained automatically by software application 166 accessing the information over network 175. In some embodiments, such environmental information is associated with the OSPRE score and/or with the patient's ultimate disposition for use in identifying relationships between certain environmental variables and a patient's likelihood of survival or developing other complications. In some embodiments, the environmental information is used in conjunction with the OSPRE score to predict, prior to arrival at the acute care facility, the intensity of care that the patient will likely require.

At a step 230, values of OSPRE variables are displayed and verified. In some embodiments, software application 166 running on mobile device 165 received data from one or more monitors 167 or other sources and displays the data for the user of the mobile device. In some embodiments, the patient data is authenticated or verified by the user as the data coming from the patient and having values that are not indicative of a malfunction or improper use of monitors(s) 167. Further, in some embodiments, the displayed data is used by the EMT/caregiver to facilitate monitoring, assessing, and caring for the patient. For example, certain data may indicate that immediate action needs to occur such as data indicating that the patient has stopped breathing or has gone into cardiac arrest.

In some embodiments, the caregiver enters the variable values into software application 166 via a GUI such as the one described in connection to FIGS. 3A and 3B. In some embodiments, the software application automatically populates these values, based on data received from the monitor(s) 167 and the caregiver verifies the populated values. As described in connection to FIG. 3A above, in some embodiments the values of data from the patient parameters are classified into zones or ordinal ranges associated with the patient parameter. Thus, in some embodiments, step 230 pertains to identifying the ordinal range that contains the value of the patient parameters identified in step 215 or 220 used for the OSPRE score.

In some embodiments (not shown), at this step, the caregiver determines which number N of patient parameters is to be used for the OSPRE score. For example, in some circumstances more patient parameters may be available from one or more monitor(s) 167, but not used for computing the OSPRE score. In some embodiments, ontology mapping or managing, which may be facilitated by ontology manager 140, is performed. For example, ontology manager 140 may be utilized for facilitating matching patient information, which may be received from different on-scene and in-transit users/caregivers, using different record systems with differing ontologies.

At a step 235, a user or caregiver performs an assessment of the patient and enters OSPRE variable values. In particular at step 235, on-scene and in-transit emergency medical staff assess and monitor the patient to obtain measurements of the parameters such as, for example, blood pressure, temperature, urine output, bleeding, and evidence of other injuries. In some embodiments, a caregiver completes an assessment using a form such as the form provided by GUI 300 in FIG. 3A, which includes assessing item values for fourteen patient parameters. Some of these parameters, such as those associated with perfusion and cardiac functions 322 and oxygenation and respiratory functions 324, are derived from patient monitor(s) 167 and may be populated into zones 330 automatically as described above in connection to FIG. 3A. Other patient parameters such as the trauma and tissue injury parameters are assessed by the caregiver and entered using a GUI such as GUI 300, in some embodiments. Of the hundreds of potential markers of newborn illness severity, the inventors believe that a limited subset, such as the fourteen example parameters in this embodiment (shown on the right-hand side of FIG. 3A), are reliably available, easily captured, and robust as predictors. Moreover, the inventors believe this specific list of variables, and their exact definitions, are unique to embodiments of the invention and constitute improvements over TRISS, RTL, ASCOT, or other conventional attempts at measuring illness severity.

Continuing with step 235, in some embodiments such as those described in connection to FIG. 3A, each patient parameter is associated with a multi-range ordinal series of contiguous zones covering the physiologically feasible range for each parameter, which are used for fuzzy arithmetic. In particular, in some embodiments, a reference database table (which may be embodied as a content-table parameter in a multi-agent operating system) stores an array of fuzzy weighting factors for each zone of the patient parameters. As described in step 260 and 265, the weighting factors are applied as multipliers for one or more predictive statistical equations of the endpoints or outcomes, such as a logistical regression equation for the probability of mortality within 24 hours after departing the trauma scene en route to an acute-care facility. Accordingly in assessing the patient, a caregiver selects the appropriate range. For example, for the parameter "Blunt Trauma" the caregiver selects one of the zones: absent, mild, moderate, severe-focal, and severe-extensive. As further described in the example embodiments of FIG. 3A, five zones or ordinal ranges are indicated in this embodiment for practicality and simplicity, but other embodiments may include more or fewer zones.

Although the "perform assessment" step 235 is shown as a single step in method 200, it is contemplated that in some embodiments the caregiver is continuously assessing the patient and may be continuously updating the values of patient parameters via a GUI 300 of application 166 on mobile device 165, for example. For example, in subsequent OSPRE entries, at step 235, the user/caregiver may update the values of patient parameters. Similarly, in some embodiments data from patient monitor(s) 167 continues to be received.

At a step 240, an OSPRE entry is stored. In some embodiments, step 240 includes verifying the OSPRE entry is completed, such as verifying that all of the necessary the data has been received, storing the entry on mobile device 165 and communicating the entry to a Hospital EHR system, such as EHR systems 161 and 163, and to a remote OSPRE server, which may be embodied as computer system 120. In some embodiments, individual values of patient parameters are collected and registered on the computerized patient records or EHR systems, such as on a tablet computer connected to the remote electronic medical record via an RF telecommunications link. For example, periodically at time intervals T, all or a collection of readings of the parameters are obtained, entered, and transmitted to the remote computer. A measured parameter may have several recorded values in a specified time interval T, as discussed in step 225. As described above, in some embodiments, time interval T, which might be 5 minutes or 10 minutes, corresponding to the duration of an OSPRE entry. In some embodiments T is determined as a time interval that provides an appropriate and representative period for receiving information of the patient's condition by a caregiver or attending emergency medical staff or based on time-to-arrival at an acute-care facility. Time interval T may be determined from a user or caregiver, a pre-configured setting, or by software application 166, by an agent operating in a multi-agent computer system 120, for example based one or more factors such as the patient's condition, time to arrival at an acute-care facility, specific patient parameters which are being measured. In some embodiments, software application 166 determines interval T and a user/caregiver, which may be a local user or backend user, confirms the interval.

In some embodiments, patient information acquired for each OSPRE entry is used to determine a partial OSPRE score and/or 24-hour mortality probability in accordance with steps 255 through 270 of FIG. 2B. The partial score and probability can be updated with each successive OSPRE entry taken. In some embodiments, the total number of OSPRE entries taken is dependent on the time to transport the patient to an acute care facility. For example, if the time interval for taking an OSPRE entry is 10 minutes, and the estimated time to arrival at a hospital is 45 minutes, then it can be expected that there will be time for completing four OSPRE entries. With each additional OSPRE entry taken, the score and probability can be recomputed and updated until the patient arrives at the acute care facility, at which time a final score and probability may be determined. In some embodiments, updating the OSPRE score and probability considers the total data acquired over all previous OSPRE entries in a session, rather than replacing the score and probability based on the values of the most recent OSPRE entry.

At steps 245 and 250 it is determined whether the patient has arrived at the acute care facility and whether there is time for adding another OSPRE entry. Specifically, at step 245 if the patient has arrived at a hospital or acute care facility, then the method proceeds to a step 255. If not, then the method proceeds to step 250, where it is determined whether to add another OSPRE entry. In some embodiments, at step 250 another OSPRE entry is added if there is time for taking an entry before arriving at the acute care facility. In some embodiments, software application 166 interrogates the user about whether to take another OSPRE entry. In some embodiments, the decision to take another entry is based on the time interval T for taking an entry and the estimated time-until-arrival at the acute care facility. In particular, in some embodiments, mobile device 165 determines an estimated time of arrival based on the location and velocity of the device 165 and location information of the acute care facility, which may be provided by the device user or accessed over network 175, based on the emergency response information associated with the patient. Accordingly, if there is 20 minutes estimated until arrival, and time interval T is 10 minutes, then another OSPRE entry may be performed and the method returns to step 220. However, if there is only 3 minutes estimated until arrival, then the method proceeds to step 255. In some embodiments, the estimated time of arrival may be updated en route and may result in time for additional OSPRE entries. For example, an initial estimated time-until-arrival for ambulance transporting a patient to a hospital may be 35 minutes, but if the ambulance encounters unexpectedly heavy traffic, this time of arrival may be updated en route.

If it is determined that another OSPRE entry is to be taken, then the method returns to step 220. Otherwise, the method continues to step 255.

At step 255, OSPRE entries are finalized. In some embodiments, values of OSPRE entries are accessed and prepared for applying fuzzy arithmetic in step 260. In some embodiments, the measured values of the OSPRE entries are used to generate an optimal value for each measured parameter, which may be used to produce a modified weighted partial score for each parameter, in one embodiment.

At a step 260, fuzzy means are determined for the patient parameters. In some embodiments, a fuzzy means is calculated for each of the OSPRE variables for all of the OSPRE entries. In some embodiments, a reference database table (which may be embodied as a content-table parameter in a multi-agent operating system) stores an array of fuzzy weighting factors for each ordinal-range zone 330 of the patient parameters. The weighting factors of the array are applied as multipliers for one or more predictive statistical equations of the endpoints or outcomes, such as a logistical regression equation for the probability of mortality within 24 hours after departing the trauma scene en route to an acute-care facility.

In particular, each zone of the multi-range ordinal zones of N patient parameters, is associated with a convex polygonal fuzzy number 2-dimensional array where the first column of the array contains a vector of feasible abscissa values that the parameter may take on and the second column contains numeric plausibility values ranging from 0.0 to 1.0 denoting the degree of membership in the zone for each abscissa value row.

Additionally, in some embodiments, a measured parameter may have several recorded values over the time interval in which it was recorded within an entry. The worst value, for example, may be selected using carefully defined predetermined criteria. The degree of derangement is ascertained and a partial score is assigned for each parameter. In some embodiments, each parameter variable is weighted according to a carefully derived risk-predictive statistical equation, so that less serious items have relatively low score points, and more serious items have relatively high score points.

The weighting consists of computing the fuzzy mean of the plurality of observations entered for each variable. In one embodiment, the software package SACD, in R-system of software package 126 is used to perform the fuzzy arithmetic by providing polygonal fuzzy arithmetic operators (such as sum, Hukuhara difference, scalar product, mean, quintiles) and providing Bertoluzza distance, sample variance, sample covariance, and sample correlation. The fuzziness of each parameter variable and the fuzziness of each "level" or membership level within each variable, can all be different from one another, according to empirical physiology in casemix encountered, and according to user epistemology, observational psychology, or medical nuances, for example. Thus fuzzy math effectively combines the assessed patient data provided by multiple observers who are not entirely agreeing with each other or who are attending to the patient during separate time intervals. In some embodiments, fuzzy arithmetic of step 260 is facilitated by one or more software agents, operating in a multi-agent operating system 129.

At a step 265, the OSPRE score and post 24-hour probability of mortality are determined. The fuzzy means determined in step 260 are "defuzzied," with the equation as described above, and used for determining the illness severity score and probability of mortality and as input to the OSPRE predictive statistical equations. In some embodiments, the OSPRE score is determined as the sum of defuzzified fuzzy means, and in some embodiments, the weighting factors are applied as multipliers for one or more predictive statistical equations of the endpoints or outcomes, such as a logistical regression equation for the probability of mortality within 24 hours after departing the trauma scene en route to an acute-care facility. For example in one embodiment, the probability of mortality 24 hours post arrival is determined as $\text{Prob}(\text{mortality})=\exp(R)/(1+\exp(R))$, where R is the logistic regression linear combination with beta coefficients as calculated using the defuzzying equation on the fuzzy means determined in step 260.

In particular, quantitative evidence-combining is performed by fuzzy math operations on the fuzzy parameter measurements and defuzzification to produce final crisp values for the net assembly or aggregation of these, reflecting a plurality of observations over 10 or more minutes. In embodiments, equations associating the OSPRE score (or its individual components) with an array of outcomes, resource use, costs and process benchmarks are derived from regression equations (linear, logistic, polynomial) through a model-fitting process that involves modification of the input variables and selective inclusion to optimize the discrimination and calibration of the equations.

In some embodiments, the linear regression models applied in step 265 may be calibrated or recalibrated based on environmental parameters (such as whether the patient was transported by air or ground).

At a step 270, OSPRE score is verified and displayed. In some embodiments this is facilitated by a GUI such as GUI 300 operating on a software application 166, and verified by a user or caregiver operating mobile device 165. In some embodiments, the illness severity score is displayed and may be compared with other known values, such as previous OSPRE score values or other OSPRE values. In some embodiments, these OSPRE score values are calculated from earlier OSPRE entries carried out by the same user/caregiver as the present OSPRE score, or may be other OSPRE values associated with the same date-time coordinate calculated from OSPRE entries carried out by user/caregivers different from the one associated with the current displayed OSPRE score. In other words, different user/caregivers may not uniformly agree on what parameters are to be measured or may be unable to measure the same parameters as other user/caregivers. For example, one caregiver might not move the patient's head at a particular time, out of concern for spinal cord injury, and as a result might at that time not have the opportunity to observe blunt trauma to the back of the head, which was not visible to that caregiver; whereas, to another caregiver who was able to visualize the back of the head, the entry of 'head trauma' into OSPRE may be possible. Accordingly, some embodiments tolerate or support this sort of 'multi-vocality' of scores. Moreover, in these embodiments, the combined appreciation of score diversity across observers and trending across time affords a more reliable assessment of severity than any one observation, data-entry source, or 'voice' would provide.

At a step 275, the OSPRE score, mortality probability, and in some embodiments the user verification, are stored. In some embodiments, these items are stored on data store 121 or otherwise communicated to an EHR systems 161 or 163 and to a remote OSPRE server, which may be embodied as computer system 120. In some embodiments, at least steps 260 through 270 are facilitated by a remote OSPRE server communicating with mobile device 165. Furthermore, in some embodiments, display or verification at step 270 occurs at the hospital or at an acute care facility and may also be used for scheduling resources for treating the patient, for example.

In some embodiments, a misclassification rate and statistical sensitivity may be determined based on the resulting mortality of the patient, and used to refine subsequent determinations of OSPRE score and mortality probability. For example, Table 1 shows an OSPRE validation cohort having Sensitivity=79%; Specificity=92%; Misclassification=11%, and Mortality prevalence=24%.

| OSPRE validation cohort | | |
| --- | --- | --- |
|  | Expired | Survived |
| OSPRE p(mort 24 h) > 0.80 | 19 | 6 |
| OSPRE p(mort 24 h) ≤ 0.80 | 5 | 70 |

FIGS. 4A and 4B depict screen shots of GUI from an embodiment of the invention reduced to practice, with a GUI implemented in Microsoft Excel. The screenshots of the GUI in FIGS. 4A and 4B is similar to example GUI 300 described in connection to FIG. 3A. Specifically, FIG. 4A depicts a completed assessment with a computed OSPRE score and mortality probability. FIG. 4B depicts an incomplete assessment, having a missing a parameter entry and a duplicated parameter entry, and without a computed OSPRE score and mortality probability.

With reference to FIGS. 4A and 4B, columns 425 and 423 are shown which include a scoring and validation of the patient parameters 420 assessed by a caregiver. In particular, column 425 includes "YES" entries which validate that an assessment has been entered for the parameter associated with that particular row. Similarly, column 423 computes a partial score based on the parameter and ordinal range. Where data is missing (429 of FIG. 4B) or duplicative (427 of FIG. 4B), an error is reported. For example, "NO" appears instead of YES, in column 425, and a "check data" appears in column 423. Similarly, "Data Complete" 453 reports "NO" indicating that data is missing, and "Evaluation appropriate" 455 indicates incomplete data. Moreover, the example of FIG. 4B also shows incomplete data for score 462 or "#Value" (indicating a missing value in Excel) for the OSPRE score 465 and mortality probability 471.

With further reference to FIG. 4A, "YES" entries in column 425 are determined based on the following excel equation, with respect to the heart rate parameter (first row): =IF(IF(NOT(ISBLANK(B9)),1,0)+IF(NOT(ISBLANK(C9)),1,0)+IF(NOT(ISBLANK(D9)),1, 0)+IF(NOT(ISBLANK(E9)),1,0)+IF(NOT(ISBLANK(F9)),1,0)= 1,"Yes","No"). With reference to the same row, number scores of column 423 may be computed as: =IF(G9="No", "check data", IF(NOT(ISBLANK(B9)),0,0)+IF(NOT(ISBLANK(C9)),1,0)+IF(NOT(ISBLANK(D9)), 2,0)+IF(NOT(ISBLANK(E9)),3,0)+IF(NOT(ISBLANK(F9)),4,0)).

Continuing with the example of FIG. 4A, Data Complete 452 may be determined as: =IF(OR(ISBLANK(B2),ISBLANK(B3),ISBLANK(B4),G9="No",G11="No", G13="No",G15="No", G18="No",G20="No",G22="No", G25="No", G27="No", G29="No", G31="No", G33="No", G35="No", G38="No"), "No","Yes"). Evaluation Appropriate 454 may be determined as: =IF(B41="No","complete data",IF(B2="Y","Yes","No")). The value displayed in OSPRE Score 462 may be determined as: =IF(B41="No", "complete data", SUM(H9:H38)), and the value displayed by Mortality probability 470 as:
=EXP(E39+H3+F39*H4+G39*H39)/(1+EXP(E39+H3+F39*H4+G39*H39)), wherein E39 is given as: −3.703; F39 is given as 0.12; G39 is given as 6.452; B39 is the (OSPRE score)/56, where 56 is the maximum here; H3=IF(B3="Y", 0,0.235); B3 indicates whether the patient's age is between 10 and 70 years old; H4=POWER(1.02,MAX(1,INT(B4/10))); and B4 is the expected transport time in minutes.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the claims.

The invention claimed is:

1. A system that provides decision support assistance during a transportation of a patient to an acute care facility, the system comprising:
　a portable wearable monitor to receive one or more measured values for one or more physiological parameters within a timespan that is prior to arriving a health care facility, the one or more physiological parameters comprising a first physiological parameter and a second physiological parameter; and
　a mobile device that communicates with the portable wearable monitor, wherein the mobile device comprises a multi-agent trauma illness-severity decision support system having at least one service that is distributed across a plurality of computing devices in a cloud or one or more physical locations to facilitate distribution of patient information, wherein a distributed runtime service determines a quantitative numerical score of illness severity and calculated probabilities of deterioration and/or mortality, based on multi-variable statistical regressions,
　wherein the multi-agent trauma illness-severity decision support system performs a method of:
　　determining a first set of information based on measurements from the portable wearable monitor, the first set of information including a first measured value for the first physiological parameter and a second measured value for the second physiological parameter;
　　determining a contiguous zone for the first measured value and a contiguous zone for the second measured value, wherein each contiguous zone is associated with a fuzzy weighting factor;
　　for each physiological parameter, determining a zone corresponding to an optimal value of the physiological parameter and identifying the fuzzy weighting factor attributed to the zone;
　　based on the optimal value, determining a modified weighted partial value for each measured value received from the portable wearable monitor;
　　utilizing a combination of (i) a defuzzification of the modified weighted partial value for the first physiological parameter and (ii) a defuzzification of the modified weighted partial value for the second physiological parameter as an indication of trauma illness-severity and allocating resources, in near real-time, for treating the patient upon arrival at the health care facility;
　　automatically populating one or more values in one or more zones based on the one or more measured values from the portable wearable monitor;
　　displaying, on a GUI, the automatically populated one or more values in the one or more zones; and
　　determining a time until arrival at the health care facility, and if the time until arrival is greater than the timespan, then:
　　　receiving over the timespan a second set of information about a condition of the patient, wherein the second set of information received comprises one or more measured values of patient parameters;
　　　based on an optimal value, determining a modified weighted partial score for each patient parameter based on each measured value of the first set of information and the second set of information; and
　　　determining an updated indication of trauma illness-severity by quantitatively combining the modified weighted partial scores.

2. A system comprising:
　a remote computer at a health care facility that allocates resources for treating patients at the health care facility; and
　a computerized device comprising:
　　one or more processors; and
　　computer storage memory having computer-executable instructions stored thereon which, when executed by the one or more processors, implement a method of determining trauma illness-severity of a patient, the method comprising:
　　　determining, via a multi-agent operating system that provides at least one service that is distributed across the remote computer and the computerized device in a cloud or physical location to facilitate distribution of patient information, a first set of information based on measurements from a portable wearable monitor having a sensor that performs a physical measurement of the patient during a timespan that is prior to the patient arriving at the health care facility, the first set of information comprising one or more values for a plurality of patient parameters, wherein a distributed runtime service determines a quantitative numerical score of illness severity and calculated probabilities of deterioration and/or mortality, based on multi-variable statistical regressions;
　　　determining, via the multi-agent operating system, a contiguous zone for the one or more values, wherein the contiguous zone is one of a plurality of contiguous zones that are each associated with a fuzzy weighting factor;
　　　determining, via the multi-agent operating system, a fuzzy mean for the one or more values based on the contiguous zone and the fuzzy weighting factor;
　　　utilizing a defuzzification of the fuzzy mean as an indication of trauma illness-severity and instructing, in near real-time, the remote computer at the health care facility to allocate resources for treating the patient upon arrival at the health care facility;
　　　automatically populating one or more values in one or more zones based on the one or more measured values from the portable wearable monitor;
　　　displaying, on a GUI, the automatically populated one or more values in the one or more zones; and
　　　determining a time until arrival at the health care facility, and if the time until arrival is greater than the timespan, then:
　　　　receiving over the timespan a second set of information about a condition of the patient, wherein the second set of information received comprises one or more measured values of patient parameters;
　　　　based on an optimal value, determining a modified weighted partial score for each patient parameter based on each measured value of the first set of information and the second set of information; and determining an updated indication of trauma illness-severity by quantitatively combining the modified weighted partial scores.

3. The system of claim 2, wherein the fuzzy weighting factor is calibrated based on an environmental factor associated with transporting the patient to the health care facility.

4. The system of claim 2, wherein the first set of information about a condition of the patient, in addition to the measurements from the portable wearable monitor, is also based on information about the condition received from a plurality of caregivers that is processed by an ontology manager that includes one or more agents operating on the multi-agent operating system, wherein the ontology manager matches differing ontologies associated with the information received from the plurality of caregivers.

5. The system of claim 2, wherein the method further comprises:

automatically receiving measurements, during the timespan that is prior to the patient arriving at the health care facility, from a second wearable monitor for determining the first set of information, wherein the second wearable monitor comprises a second sensor that performs a second physical measurement of the patient.

6. The system of claim 2, wherein the method further comprises determining a mortality risk level associated with the patient from the updated indication of trauma illness-severity.

7. The system of claim 2, wherein the method further comprises:

determining a measure of improvement or deterioration in the condition of the patient by comparing the updated indication of trauma illness-severity associated with the patient with the indication of trauma illness-severity.

8. A computer software program operating on a computer system to facilitate triage of patients for entry into a health care emergency department, the computer software program comprising computer-executable instructions that when executed by a processor of the computer system, perform operations comprising:

determining a first set of information based on measurements from a portable wearable monitor having a sensor that performs a physical measurement of a patient during a timespan that is prior to the patient arriving at a health care facility, wherein the first set of information comprises one or more values for a plurality of patient parameters;

determining a contiguous zone for the one or more values, wherein the contiguous zone is one of a plurality of contiguous zones that are each associated with a fuzzy weighting factor;

determining a fuzzy mean for the one or more values based on the contiguous zone and the fuzzy weighting factor;

defuzzying the fuzzy mean and providing, over a cloud service that is distributed across the computer system and the portable wearable monitor to facilitate distribution of patient information, the defuzzied mean for display on a graphical user interface, the defuzzied mean displayed as an indication of trauma illness-severity for allocating resources, in near real-time, for treating the patient upon arrival at the health care facility, wherein a distributed runtime service determines a quantitative numerical score of illness severity and calculated probabilities of deterioration and/or mortality, based on multi-variable statistical regressions;

automatically populating one or more values in one or more zones based on the one or more measured values from the portable wearable monitor; and displaying, on a GUI, the automatically populated one or more values in the one or more zones; and determining a time until arrival at the health care facility, and if the time until arrival is greater than the timespan, then:

receiving over the timespan a second set of information about a condition of the patient, wherein the second set of information received comprises one or more second values for the plurality of patient parameters;

for each of the plurality of patient parameters, determining the fuzzy mean of the values associated with that parameter based on the first set of information and the second set of information; and determining an updated indication of trauma illness-severity associated with the patient by defuzzying and combining each fuzzy mean.

9. The computer software program of claim 8, wherein the operations further comprise determining a mortality risk level associated with the patient from the indication of trauma illness-severity.

10. The computer software program of claim 8, wherein the first set of information corresponds to a condition of the patient, wherein the measurements are received from a plurality of sensors via a plurality of on-scene or in-transit caregivers.

11. The computer software program of claim 8, wherein the operations further comprise:

automatically receiving during the timespan one or more measured values of patient parameters from a second patient monitor, wherein the second patient monitor comprises another sensor that performs another physical measurement of the patient.

12. The computer software program of claim 8, wherein the fuzzy weighting factor is determined by logistic regression.

13. The computer software program of claim 8, wherein the plurality of patient parameters include: heart rate; T-minute heart rate variability, systolic blood pressure, T-minute systolic blood pressure variability; respiratory rate (spontaneous breathing); T-minute respiratory rate variability, peripheral oxygen saturation ($SpO_2$);

wherein the plurality of patient parameters further include an assessment of a presence and severity of penetrating trauma by physical examination; an assessment of a likelihood and severity of blunt trauma by physical examination; an assessment of a presence and severity of burns of skin and soft tissue by physical examination; an assessment of a likelihood and severity of systemic thermal stress (hypothermia or hyperthermia) by physical examination and by measuring the patient's temperature; an assessment of external evidence of a presence and severity of inhalation injury by physical examination, such as by chemical fumes or smoke or hot gases in a fire; an assessment by physical examination, of external evidence of a presence and severity of traumatic brain injury; and Reaction Level Scale (RLS85);
wherein T is at least 5 minutes; and
wherein the systolic blood pressure is measured at a sampling frequency of not less than two times per minute.

14. The computer software program of claim 13, wherein T is equal to the timespan for receiving information about a patient's condition.

15. The computer software program of claim 8, wherein the timespan is determined based on an estimated arrival time of the patient to the health care facility.

16. The computer software program of claim 8, wherein the operations further comprise determining a mortality risk level associated with the patient from the updated indication of trauma illness-severity.

17. The computer software program of claim 16, wherein the operations further comprise:
  determining a measure of improvement or deterioration in the condition of the patient by comparing the updated indication of trauma illness-severity associated with the patient with the indication of trauma illness-severity.

18. The system of claim 1, wherein the fuzzy weighting factor is calibrated based on an environmental factor associated with transporting the patient to the health care facility.

19. The method according to claim 1, wherein an OSPRE runtime service is configured on run on the system to facilitate receiving patient information.

* * * * *